US011648274B2

(12) United States Patent
Pulé et al.

(10) Patent No.: US 11,648,274 B2
(45) Date of Patent: May 16, 2023

(54) POLYPEPTIDE

(71) Applicant: AUTOLUS LIMITED, London (GB)

(72) Inventors: Martin Pulé, London (GB); Matteo Righi, London (GB); Simon Thomas, London (GB); Shimobi Onuoha, London (GB); Shaun Cordoba, London (GB)

(73) Assignee: AUTOLUS LIMITED, London (GB)

( * ) Notice: Subject to any disclaimer, the term of this patent is extended or adjusted under 35 U.S.C. 154(b) by 286 days.

(21) Appl. No.: 16/766,128

(22) PCT Filed: Nov. 23, 2018

(86) PCT No.: PCT/GB2018/053390
§ 371 (c)(1),
(2) Date: May 21, 2020

(87) PCT Pub. No.: WO2019/102207
PCT Pub. Date: May 31, 2019

(65) Prior Publication Data
US 2020/0360432 A1 Nov. 19, 2020

(30) Foreign Application Priority Data

Nov. 24, 2017 (GB) ..................................... 1719557

(51) Int. Cl.
*A61K 35/17* (2015.01)
*C07K 14/725* (2006.01)
*C07K 14/715* (2006.01)
(52) U.S. Cl.
CPC .......... *A61K 35/17* (2013.01); *C07K 14/7051* (2013.01); *C07K 14/7155* (2013.01); *C07K 2319/03* (2013.01)

(58) Field of Classification Search
CPC ............ A61K 35/17; A61K 2039/5158; C07K 14/7051; C07K 14/7155; C07K 2319/03; C07K 2319/00
See application file for complete search history.

(56) References Cited

U.S. PATENT DOCUMENTS

| 6,323,027 B1 | 11/2001 | Burkly et al. |
| 2018/0244797 A1 | 8/2018 | Pule et al. |
| 2019/0016820 A1 | 1/2019 | Pule et al. |

FOREIGN PATENT DOCUMENTS

| WO | WO-2013123061 A1 * | 8/2013 | ............. A61K 35/17 |
| WO | WO-2017/029512 A1 | 2/2017 | |

OTHER PUBLICATIONS

Emmons, K. M., et al (Mar. 2017) Realizing the Potential of Cancer Prevention—The Role of Implementation Science N Engl J Med 376(10); 986-990 (Year: 2017).*

(Continued)

*Primary Examiner* — Joanne Hama
*Assistant Examiner* — Audrey L Buttice
(74) *Attorney, Agent, or Firm* — Marshall, Gerstein & Borun LLP

(57) ABSTRACT

The present invention provides a chimeric polypeptide comprising: an antigen-binding domain which constitutively binds to an ectodomain of a first chain of a cytokine receptor; a transmembrane domain; and an endodomain from a second chain of the cytokine receptor which chimeric polypeptide, when expressed in a cell, binds to the endogenous first chain of the cytokine receptor causing constitutive cytokine signalling.

29 Claims, 4 Drawing Sheets
Specification includes a Sequence Listing.

A

B

(56) References Cited

OTHER PUBLICATIONS

Cuzick, J. (Aug. 2017) Preventive therapy for cancer Lancet Oncol 18; e472-e482 (Year: 2017).*
Leen, A.M., et al (2014) Reversal of Tumor Immune Inhibition Using a Chimeric Cytokine Receptor Molecular Therapy 22(6) 1211-1220 (Year: 2014).*
Martin, C.E., et al (2013) IL-7/anti-IL-7 mAb complexes augment cytokine potency in mice through association with IgG-Fc and by competition with IL-7R Blood 121(22); 4484-4492 (Year: 2013).*
Shi, H., et al (2014) Chimeric antigen receptor for adoptive immunotherapy of cancer: latest research and future prospects Molecular Cancer 13(219); 1-8 (Year: 2014).*
Esen, I. (2015) The Structure and Signaling Mechanisms of Type 1 Cytokine Receptors: A Brief Overview Turk J Immunol 3(3); 121-124 (Year: 2015).*
Spangler, J.B., et al (2015) Insights into Cytokine-Receptor Interactions from Cytokine Engineering Annu Rev Immunol 33; 139-167 (Year: 2015).*
Finkelman, F.D., et al (1993) Anti-Cytokine Antibodies as Carrier Proteins Journal of Immunology 151; 1235-1244 (Year: 1993).*
Jiang, Q., et al (2004) Distinct Regions of the Interleukin-7 Receptor Regulate Different Bcl2 Family Members Molecular and Cellular Biology 24(14); 6501-6513 (Year: 2004).*
Wilkie, S., et al (2010) Selective Expansion of Chimeric Antigen Receptor-targeted T cells with Potent Effector Function using Interleukin-4 Journal of Biological Chemistry 285(33) 25538-25544 (Year: 2010).*
Hunter, M.R., et al (2013) Chimeric γc cytokine receptors confer cytokine independent engraftment of human T lymphocytes Molecular Immunology 56; 1-11 (Year: 2013).*
Ussar, S., et al (2011) Receptor Antibodies as Novel Therapeutics for Diabetes Science Translational Medicine 3(113); 1-3 (Year: 2011).*
U.S. Appl. No. 15/753,486, filed Feb. 19, 2018, US 2018-0244979.
U.S. Appl. No. 16/113,224, filed Aug. 27, 2018, US 2019-0016820.
Donnelly et al., "The 'cleavage' activities of foot-and-mouth disease virus 2A site-directed mutants and naturally occurring '2A-like' sequences," J. Gen. Virol. 82:1027-1041 (2001).
Hassuneh et al., "Evidence for the Participation of Interleukin-2 (IL-2) and IL-4 in the Regulation of Autonomous Growth and Tumorigenesis of Transformed Cells of Lymphoid Origin," Blood 89:610-620 (1997).
International Search Report and Written Opinion from International Application No. PCT/GB2018/053390 dated Feb. 12, 2019.
Nagarkatti et al., "Constitutive activation of the interleukin 2 gene in the induction of spontaneous in vitro transformation and tumorigenicity of T cells," PNAS 91:7638-7642 (1994).
Shum et al., "Constitutive Signaling from an Engineered IL7 Receptor Promotes Durable Tumor Elimination by Tumor-Redirected T Cells," Cancer Discovery 7(11):1238-1247 (2017).
Sogo et al., "Selective expansion of genetically modified T cells using an antibody/interkeulin-2 receptor chimera," Journal of Immunological Methods 337(1):16-23 (2008).

* cited by examiner

```
                          SEQUENCE LISTING

<160> NUMBER OF SEQ ID NOS: 33

<210> SEQ ID NO 1
<211> LENGTH: 86
<212> TYPE: PRT
<213> ORGANISM: Artificial Sequence
<220> FEATURE:
<223> OTHER INFORMATION: Endodomain derived from human common gamma
      chain

<400> SEQUENCE: 1

Glu Arg Thr Met Pro Arg Ile Pro Thr Leu Lys Asn Leu Glu Asp Leu
1               5                   10                  15

Val Thr Glu Tyr His Gly Asn Phe Ser Ala Trp Ser Gly Val Ser Lys
            20                  25                  30

Gly Leu Ala Glu Ser Leu Gln Pro Asp Tyr Ser Glu Arg Leu Cys Leu
        35                  40                  45

Val Ser Glu Ile Pro Pro Lys Gly Gly Ala Leu Gly Glu Gly Pro Gly
    50                  55                  60

Ala Ser Pro Cys Asn Gln His Ser Pro Tyr Trp Ala Pro Pro Cys Tyr
65                  70                  75                  80

Thr Leu Lys Pro Glu Thr
                85

<210> SEQ ID NO 2
<211> LENGTH: 286
<212> TYPE: PRT
<213> ORGANISM: Artificial Sequence
<220> FEATURE:
<223> OTHER INFORMATION: Endodomain derived from human IL-2Rbeta

<400> SEQUENCE: 2

Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
        35                  40                  45

Ser Pro Gly Gly Leu Ala Pro Glu Ile Ser Pro Leu Glu Val Leu Glu
    50                  55                  60

Arg Asp Lys Val Thr Gln Leu Leu Leu Gln Gln Asp Lys Val Pro Glu
65                  70                  75                  80
```

```
Pro Ala Ser Leu Ser Ser Asn His Ser Leu Thr Ser Cys Phe Thr Asn
                85                  90                  95

Gln Gly Tyr Phe Phe Phe His Leu Pro Asp Ala Leu Glu Ile Glu Ala
            100                 105                 110

Cys Gln Val Tyr Phe Thr Tyr Asp Pro Tyr Ser Glu Glu Asp Pro Asp
            115                 120                 125

Glu Gly Val Ala Gly Ala Pro Thr Gly Ser Ser Pro Gln Pro Leu Gln
130                 135                 140

Pro Leu Ser Gly Glu Asp Asp Ala Tyr Cys Thr Phe Pro Ser Arg Asp
145                 150                 155                 160

Asp Leu Leu Leu Phe Ser Pro Ser Leu Leu Gly Gly Pro Ser Pro Pro
                165                 170                 175

Ser Thr Ala Pro Gly Gly Ser Gly Ala Gly Glu Glu Arg Met Pro Pro
                180                 185                 190

Ser Leu Gln Glu Arg Val Pro Arg Asp Trp Asp Pro Gln Pro Leu Gly
                195                 200                 205

Pro Pro Thr Pro Gly Val Pro Asp Leu Val Asp Phe Gln Pro Pro Pro
                210                 215                 220

Glu Leu Val Leu Arg Glu Ala Gly Glu Glu Val Pro Asp Ala Gly Pro
225                 230                 235                 240

Arg Glu Gly Val Ser Phe Pro Trp Ser Arg Pro Pro Gly Gln Gly Glu
                245                 250                 255

Phe Arg Ala Leu Asn Ala Arg Leu Pro Leu Asn Thr Asp Ala Tyr Leu
                260                 265                 270

Ser Leu Gln Glu Leu Gln Gly Gln Asp Pro Thr His Leu Val
                275                 280                 285

<210> SEQ ID NO 3
<211> LENGTH: 195
<212> TYPE: PRT
<213> ORGANISM: Artificial Sequence
<220> FEATURE:
<223> OTHER INFORMATION: Endodomain derived from human IL-7Ralpha

<400> SEQUENCE: 3

Lys Lys Arg Ile Lys Pro Ile Val Trp Pro Ser Leu Pro Asp His Lys
1               5                   10                  15

Lys Thr Leu Glu His Leu Cys Lys Lys Pro Arg Lys Asn Leu Asn Val
                20                  25                  30

Ser Phe Asn Pro Glu Ser Phe Leu Asp Cys Gln Ile His Arg Val Asp
            35                  40                  45

Asp Ile Gln Ala Arg Asp Glu Val Glu Gly Phe Leu Gln Asp Thr Phe
    50                  55                  60

Pro Gln Gln Leu Glu Glu Ser Glu Lys Gln Arg Leu Gly Gly Asp Val
65                  70                  75                  80

Gln Ser Pro Asn Cys Pro Ser Glu Asp Val Val Ile Thr Pro Glu Ser
                85                  90                  95

Phe Gly Arg Asp Ser Ser Leu Thr Cys Leu Ala Gly Asn Val Ser Ala
            100                 105                 110

Cys Asp Ala Pro Ile Leu Ser Ser Ser Arg Ser Leu Asp Cys Arg Glu
            115                 120                 125

Ser Gly Lys Asn Gly Pro His Val Tyr Gln Asp Leu Leu Leu Ser Leu
130                 135                 140
```

-continued

Gly Thr Thr Asn Ser Thr Leu Pro Pro Phe Ser Leu Gln Ser Gly
145                 150                 155                 160

Ile Leu Thr Leu Asn Pro Val Ala Gln Gly Gln Pro Ile Leu Thr Ser
                165                 170                 175

Leu Gly Ser Asn Gln Glu Glu Ala Tyr Val Thr Met Ser Ser Phe Tyr
            180                 185                 190

Gln Asn Gln
        195

<210> SEQ ID NO 4
<211> LENGTH: 234
<212> TYPE: PRT
<213> ORGANISM: Artificial Sequence
<220> FEATURE:
<223> OTHER INFORMATION: spacer sequence, hinge-CH2CH3 of human IgG1

<400> SEQUENCE: 4

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
                20                  25                  30

Lys Asp Thr Leu Met Ile Ala Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 5
<211> LENGTH: 46
<212> TYPE: PRT
<213> ORGANISM: Artificial Sequence
<220> FEATURE:
<223> OTHER INFORMATION: spacer sequence, human CD8 stalk

```
<400> SEQUENCE: 5

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 6
<211> LENGTH: 20
<212> TYPE: PRT
<213> ORGANISM: Artificial Sequence
<220> FEATURE:
<223> OTHER INFORMATION: spacer sequence, human IgG1 hinge

<400> SEQUENCE: 6

Ala Glu Pro Lys Ser Pro Asp Lys Thr His Thr Cys Pro Pro Cys Pro
1               5                   10                  15

Lys Asp Pro Lys
            20

<210> SEQ ID NO 7
<211> LENGTH: 21
<212> TYPE: PRT
<213> ORGANISM: Artificial Sequence
<220> FEATURE:
<223> OTHER INFORMATION: Transmembrane derived from human common gamma
      chain

<400> SEQUENCE: 7

Val Val Ile Ser Val Gly Ser Met Gly Leu Ile Ile Ser Leu Leu Cys
1               5                   10                  15

Val Tyr Phe Trp Leu
            20

<210> SEQ ID NO 8
<211> LENGTH: 25
<212> TYPE: PRT
<213> ORGANISM: Artificial Sequence
<220> FEATURE:
<223> OTHER INFORMATION: Transmembrane derived from human IL-2Rbeta

<400> SEQUENCE: 8

Ile Pro Trp Leu Gly His Leu Leu Val Gly Leu Ser Gly Ala Phe Gly
1               5                   10                  15

Phe Ile Ile Leu Val Tyr Leu Leu Ile
            20                  25

<210> SEQ ID NO 9
<211> LENGTH: 25
<212> TYPE: PRT
<213> ORGANISM: Artificial Sequence
<220> FEATURE:
<223> OTHER INFORMATION: Transmembrane derived from human IL-7Ralpha

<400> SEQUENCE: 9

Pro Ile Leu Leu Thr Ile Ser Ile Leu Ser Phe Phe Ser Val Ala Leu
1               5                   10                  15

Leu Val Ile Leu Ala Cys Val Leu Trp
            20                  25
```

```
<210> SEQ ID NO 10
<211> LENGTH: 22
<212> TYPE: PRT
<213> ORGANISM: Artificial Sequence
<220> FEATURE:
<223> OTHER INFORMATION: Transmembrane derived from human IL-15Ralpha

<400> SEQUENCE: 10

Ala Ile Ser Thr Ser Thr Val Leu Leu Cys Gly Leu Ser Ala Val Ser
1               5                   10                  15

Leu Leu Ala Cys Tyr Leu
            20

<210> SEQ ID NO 11
<211> LENGTH: 11
<212> TYPE: PRT
<213> ORGANISM: Artificial Sequence
<220> FEATURE:
<223> OTHER INFORMATION: light chain CDR, CDRL1

<400> SEQUENCE: 11

Lys Ala Ser Gln Asp Val Thr Thr Ala Val Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: light chain CDR, CDRL2

<400> SEQUENCE: 12

Trp Ala Ser Thr Arg His Thr
1               5

<210> SEQ ID NO 13
<211> LENGTH: 8
<212> TYPE: PRT
<213> ORGANISM: Artificial Sequence
<220> FEATURE:
<223> OTHER INFORMATION: light chain CDR, CDRL3

<400> SEQUENCE: 13

Gln Gln His Ile Thr Pro Trp Thr
1               5

<210> SEQ ID NO 14
<211> LENGTH: 5
<212> TYPE: PRT
<213> ORGANISM: Artificial Sequence
<220> FEATURE:
<223> OTHER INFORMATION: heavy chain CDR, CDRH1

<400> SEQUENCE: 14

Ser Tyr Gly Val His
1               5

<210> SEQ ID NO 15
<211> LENGTH: 15
<212> TYPE: PRT
<213> ORGANISM: Artificial Sequence
<220> FEATURE:
<223> OTHER INFORMATION: heavy chain CDR, CDRH2

<400> SEQUENCE: 15

Val Ile Trp Ala Gly Gly Ser Thr Asx Tyr Asn Ser Ala Leu Met
1               5                   10                  15
```

```
<210> SEQ ID NO 16
<211> LENGTH: 10
<212> TYPE: PRT
<213> ORGANISM: Artificial Sequence
<220> FEATURE:
<223> OTHER INFORMATION: heavy chain CDR, CDRH3

<400> SEQUENCE: 16

Glu Gly Ser Thr Val Asp Ser Met Asp Tyr
1               5                   10

<210> SEQ ID NO 17
<211> LENGTH: 106
<212> TYPE: PRT
<213> ORGANISM: Artificial Sequence
<220> FEATURE:
<223> OTHER INFORMATION: VL domain

<400> SEQUENCE: 17

Asp Ile Val Met Thr Gln Ser His Lys Phe Met Ser Thr Ser Val Gly
1               5                   10                  15

Asp Ser Ile Thr Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ile Thr Pro Trp
                85                  90                  95

Thr Phe Gly Gly Gly Thr Lys Leu Glu Ile
            100                 105

<210> SEQ ID NO 18
<211> LENGTH: 113
<212> TYPE: PRT
<213> ORGANISM: Artificial Sequence
<220> FEATURE:
<223> OTHER INFORMATION: VH domain

<400> SEQUENCE: 18

Leu Gln Glu Ser Gly Pro Gly Leu Val Ala Pro Gln Ser Gln Ser Leu
1               5                   10                  15

Ser Ile Thr Cys Thr Val Asp Gly Phe Ser Leu Thr Ser Tyr Gly Val
            20                  25                  30

His Trp Val Arg Gln Pro Pro Gly Lys Gly Leu Glu Trp Leu Gly Val
        35                  40                  45

Ile Trp Ala Gly Gly Ser Thr Asn Tyr Asn Ser Ala Leu Met Ser Arg
    50                  55                  60

Leu Asn Ile Asn Arg Asp Asn Ser Lys Ser Gln Ile Phe Leu Lys Met
65                  70                  75                  80

Asn Ser Leu Gln Thr Asp Asp Thr Ala Ile Tyr Tyr Cys Ala Arg Glu
                85                  90                  95

Gly Ser Thr Val Asp Ser Met Asp Tyr Trp Gly Gln Gly Thr Thr Val
            100                 105                 110

Thr
```

```
<210> SEQ ID NO 19
<211> LENGTH: 21
<212> TYPE: PRT
<213> ORGANISM: Artificial Sequence
<220> FEATURE:
<223> OTHER INFORMATION: signal peptide derived from TCR beta chain

<400> SEQUENCE: 19

Met Gly Thr Ser Leu Leu Cys Trp Met Ala Leu Cys Leu Leu Gly Ala
1               5                   10                  15

Asp His Ala Asp Gly
            20

<210> SEQ ID NO 20
<211> LENGTH: 21
<212> TYPE: PRT
<213> ORGANISM: Artificial Sequence
<220> FEATURE:
<223> OTHER INFORMATION: signal peptide derived from IgG1

<400> SEQUENCE: 20

Met Ser Leu Pro Val Thr Ala Leu Leu Leu Pro Leu Ala Leu Leu Leu
1               5                   10                  15

His Ala Ala Arg Pro
            20

<210> SEQ ID NO 21
<211> LENGTH: 20
<212> TYPE: PRT
<213> ORGANISM: Artificial Sequence
<220> FEATURE:
<223> OTHER INFORMATION: signal peptide derived from CD8a

<400> SEQUENCE: 21

Met Ala Val Pro Thr Gln Val Leu Gly Leu Leu Leu Leu Trp Leu Thr
1               5                   10                  15

Asp Ala Arg Cys
            20

<210> SEQ ID NO 22
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 22

Arg Ala Glu Gly Arg Gly Ser Leu Leu Thr Cys Gly Asp Val Glu Glu
1               5                   10                  15

Asn Pro Gly Pro
            20

<210> SEQ ID NO 23
<211> LENGTH: 19
<212> TYPE: PRT
<213> ORGANISM: Artificial Sequence
<220> FEATURE:
<223> OTHER INFORMATION: Signal Sequence from Murine heavy chain

<400> SEQUENCE: 23

Met Gly Trp Ser Cys Ile Ile Leu Phe Leu Val Ala Thr Ala Thr Gly
1               5                   10                  15

Val His Ser
```

<210> SEQ ID NO 24
<211> LENGTH: 159
<212> TYPE: PRT
<213> ORGANISM: Artificial Sequence
<220> FEATURE:
<223> OTHER INFORMATION: RQR8 marker gene sequence

<400> SEQUENCE: 24

```
Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val Arg Ala
145                 150                 155
```

<210> SEQ ID NO 25
<211> LENGTH: 17
<212> TYPE: PRT
<213> ORGANISM: Artificial Sequence
<220> FEATURE:
<223> OTHER INFORMATION: 2A peptide cleavage site sequence

<400> SEQUENCE: 25

```
Glu Gly Arg Gly Ser Leu Leu Thr Cys Gly Asp Val Glu Glu Asn Pro
1               5                   10                  15

Gly
```

<210> SEQ ID NO 26
<211> LENGTH: 20
<212> TYPE: PRT
<213> ORGANISM: Artificial Sequence
<220> FEATURE:
<223> OTHER INFORMATION: Signal sequence from mouse kappa chain

<400> SEQUENCE: 26

```
Met Glu Thr Asp Thr Leu Ile Leu Trp Val Leu Leu Leu Val Pro
1               5                   10                  15

Gly Ser Thr Gly
            20
```

<210> SEQ ID NO 27
<211> LENGTH: 108
<212> TYPE: PRT
<213> ORGANISM: Artificial Sequence
<220> FEATURE:
<223> OTHER INFORMATION: anti-gammaC Light Chain variable region -continued

<400> SEQUENCE: 27

Asp Ile Val Met Thr Gln Ser His Lys Phe Met Ser Thr Ser Val Gly
1               5                   10                  15

Asp Ser Ile Thr Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ile Thr Pro Trp
                85                  90                  95

Thr Phe Gly Gly Gly Thr Lys Leu Glu Ile Lys Arg
            100                 105

<210> SEQ ID NO 28
<211> LENGTH: 16
<212> TYPE: PRT
<213> ORGANISM: Artificial Sequence
<220> FEATURE:
<223> OTHER INFORMATION: Linker sequence

<400> SEQUENCE: 28

Ser Gly Gly Gly Gly Ser Gly Gly Gly Gly Ser Gly Gly Gly Gly Ser
1               5                   10                  15

<210> SEQ ID NO 29
<211> LENGTH: 119
<212> TYPE: PRT
<213> ORGANISM: Artificial Sequence
<220> FEATURE:
<223> OTHER INFORMATION: anti-gammaC Heavy Chain variable region

<400> SEQUENCE: 29

Gln Val Gln Leu Gln Glu Ser Gly Pro Gly Leu Val Ala Pro Gln Ser
1               5                   10                  15

Gln Ser Leu Ser Ile Thr Cys Thr Val Asp Gly Phe Ser Leu Thr Ser
            20                  25                  30

Tyr Gly Val His Trp Val Arg Gln Pro Pro Gly Lys Gly Leu Glu Trp
        35                  40                  45

Leu Gly Val Ile Trp Ala Gly Gly Ser Thr Asn Tyr Asn Ser Ala Leu
50                  55                  60

Met Ser Arg Leu Asn Ile Asn Arg Asp Asn Ser Lys Ser Gln Ile Phe
65                  70                  75                  80

Leu Lys Met Asn Ser Leu Gln Thr Asp Asp Thr Ala Ile Tyr Tyr Cys
                85                  90                  95

Ala Arg Glu Gly Ser Thr Val Asp Ser Met Asp Tyr Trp Gly Gln Gly
            100                 105                 110

Thr Thr Val Thr Val Ser Ser
        115

<210> SEQ ID NO 30
<211> LENGTH: 9
<212> TYPE: PRT
<213> ORGANISM: Artificial Sequence
<220> FEATURE:
<223> OTHER INFORMATION: HA tag sequence

```
<400> SEQUENCE: 30

Tyr Pro Tyr Asp Val Pro Asp Tyr Ala
1               5

<210> SEQ ID NO 31
<211> LENGTH: 125
<212> TYPE: PRT
<213> ORGANISM: Artificial Sequence
<220> FEATURE:
<223> OTHER INFORMATION: anti-IL2receptor beta (CD122) specific variable
      light chain

<400> SEQUENCE: 31

Met Asp Phe Gln Val Gln Ile Phe Ser Phe Leu Leu Ile Ser Ala Ser
1               5                   10                  15

Val Ile Ser Arg Gly Gln Trp Leu Thr Gln Ser Pro Val Ile Met Ser
            20                  25                  30

Ala Ser Pro Gly Glu Lys Val Thr Met Thr Cys Ser Ala Ile Ser Ser
        35                  40                  45

Ser Tyr Met Tyr Trp Tyr Gln Gln Lys Pro Gly Ser Ser Pro Arg Leu
    50                  55                  60

Leu Ile Tyr Asp Thr Ser Asn Leu Val Ser Gly Val Pro Val Arg Phe
65                  70                  75                  80

Ser Gly Ser Gly Ser Gly Thr Ser Tyr Ser Leu Thr Ile Ser Arg Met
                85                  90                  95

Glu Ala Glu Asp Ala Ala Thr Tyr Tyr Cys Gln Gln Trp Asn Thr Tyr
            100                 105                 110

Pro Tyr Thr Phe Gly Gly Gly Thr Lys Leu Glu Ile Lys
        115                 120                 125

<210> SEQ ID NO 32
<211> LENGTH: 140
<212> TYPE: PRT
<213> ORGANISM: Artificial Sequence
<220> FEATURE:
<223> OTHER INFORMATION: anti-IL2receptor beta (CD122) specific variable
      heavy chain

<400> SEQUENCE: 32

Met Lys Leu Trp Leu Asn Trp Val Phe Leu Leu Thr Leu Leu His Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Ser Asp Phe Tyr Met Glu Trp Val Arg Gln Pro Pro Gly Lys Arg Leu
    50                  55                  60

Glu Trp Ile Ala Ala Ser Arg Asn Lys Ala Asn Asp Tyr Thr Thr Glu
65                  70                  75                  80

Tyr Ser Ala Ser Val Lys Gly Arg Phe Ile Val Ser Arg Asp Thr Ser
                85                  90                  95

Gln Ser Ile Leu Tyr Leu Gln Met Asn Ala Leu Arg Ala Glu Asp Thr
            100                 105                 110

Ala Ile Tyr Tyr Cys Ala Arg Ser Tyr Arg Tyr Asp Gly Met Asp
        115                 120                 125

Tyr Trp Gly Gln Gly Thr Ser Val Thr Val Ser Ser
        130                 135                 140
```

```
<210> SEQ ID NO 33
<211> LENGTH: 5
<212> TYPE: PRT
<213> ORGANISM: Artificial Sequence
<220> FEATURE:
<223> OTHER INFORMATION: Amino acid motif (Type I cytokine receptors)
<220> FEATURE:
<221> NAME/KEY: misc_feature
<222> LOCATION: (3)..(3)
<223> OTHER INFORMATION: Xaa can be any naturally occurring amino acid

<400> SEQUENCE: 33

Trp Ser Xaa Trp Ser
1               5
```

POLYPEPTIDE

CROSS-REFERENCE TO RELATED APPLICATIONS

This is a U.S. National Phase of International Application No. PCT/GB2018/053390, filed Nov. 23, 2018, which claims priority to Great Britain Application No. 1719557.9, filed Nov. 24, 2017.

INCORPORATION BY REFERENCE OF MATERIAL SUBMITTED ELECTRONICALLY

A Sequence Listing is incorporated herein by reference as part of the disclosure. The sequence listing was submitted as a text file named "53696_Seqlisting.txt", which was created on April 30, and is 22,177 bytes in size.

FIELD OF THE INVENTION

The present invention relates to a chimeric polypeptide which, when expressed in a cell, causes constitutive cytokine signalling. The invention also relates to a cell which expresses such a chimeric polypeptide and optionally a chimeric antigen receptor or engineered T-cell receptor at the cell surface.

BACKGROUND TO THE INVENTION

Chimeric Antigen Receptors (CARs)

A number of immunotherapeutic agents have been described for use in cancer treatment, including therapeutic monoclonal antibodies (mAbs), bi-specific T-cell engagers and chimeric antigen receptors (CARs).

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals.

The most common form of these molecules are fusions of single-chain variable fragments (scFv) derived from monoclonal antibodies which recognize a target antigen, fused via a spacer and a trans-membrane domain to a signalling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

CAR T Cell Engraftment and Proliferation

Function of CAR T cells depends on survival and engraftment of the cells within the patients. In some settings, like ALL, survival of the CAR-T cells for up to 9 months appears important to prevent relapse and effect sustained remissions.

CAR T-cell persistence and survival can be enhanced by administration of cytokines. CAR-T cells have also been engineered to secrete cytokines in situ. However, there are advantages associated with both of these approaches. For example, systemic administration of cytokines can be toxic and constitutive production of cytokines may lead to uncontrolled proliferation and transformation (Nagarkatti et al (1994) PNAS 91:7638-7642; Hassuneh et al (1997) Blood 89:610-620).

An alternative approach is to engineer the cell to have a constitutive cytokine receptor. For example, WO2017/029512 describes a constitutively active cytokine-signalling chimeric transmembrane protein made by linking cytokine receptor endodomains to a "Fab" type exodomain (see FIG. 2). This structure uses the natural dimerization components of antibodies, namely the dimerization domain from the heavy and light chain constant regions. The chimeric transmembrane protein has two chains; for example, a first polypeptide which comprises the antibody light K chain and the IL2 receptor common γchain as endodomain; and a second polypeptide which comprises the antibody heavy chain CH1 and an endodomain which comprises either: the IL2 receptor β chain (giving a constitutively active IL2-signalling molecule); or the IL7 receptor (giving a constitutively active IL7-signalling molecule).

When both polypeptides are expressed in a cell, the two chains associate and form the chimeric transmembrane protein at the cell surface, providing constitutive cytokine (for example constitutive IL-2 or IL-7) signalling.

SUMMARY OF ASPECTS OF THE INVENTION

Figure 1:
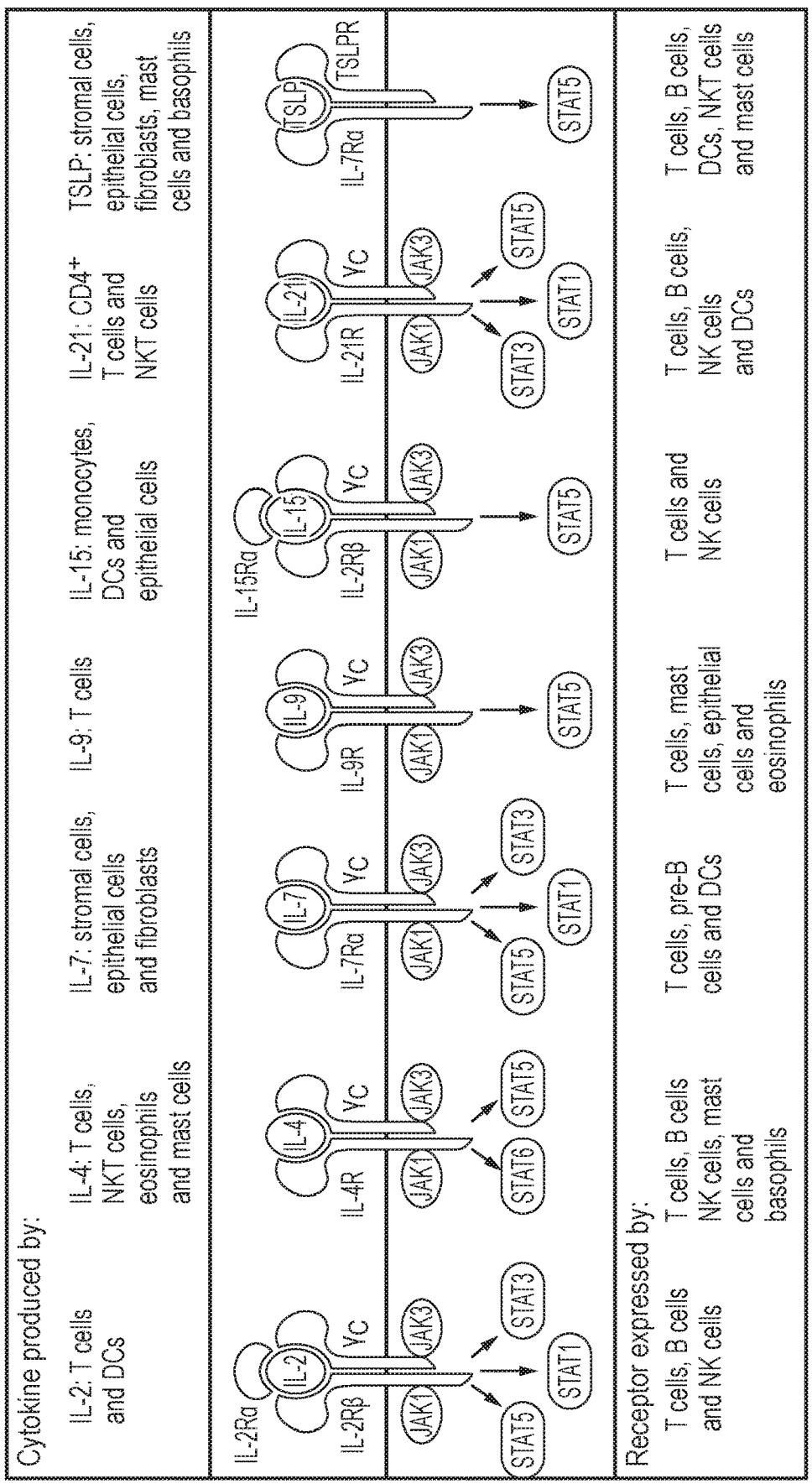
FIG. 1: Schematic diagram summarising the structure of various cytokine receptors, the cell types which produce the cytokines and the cell types which express the cytokine receptors.
Figure 2:
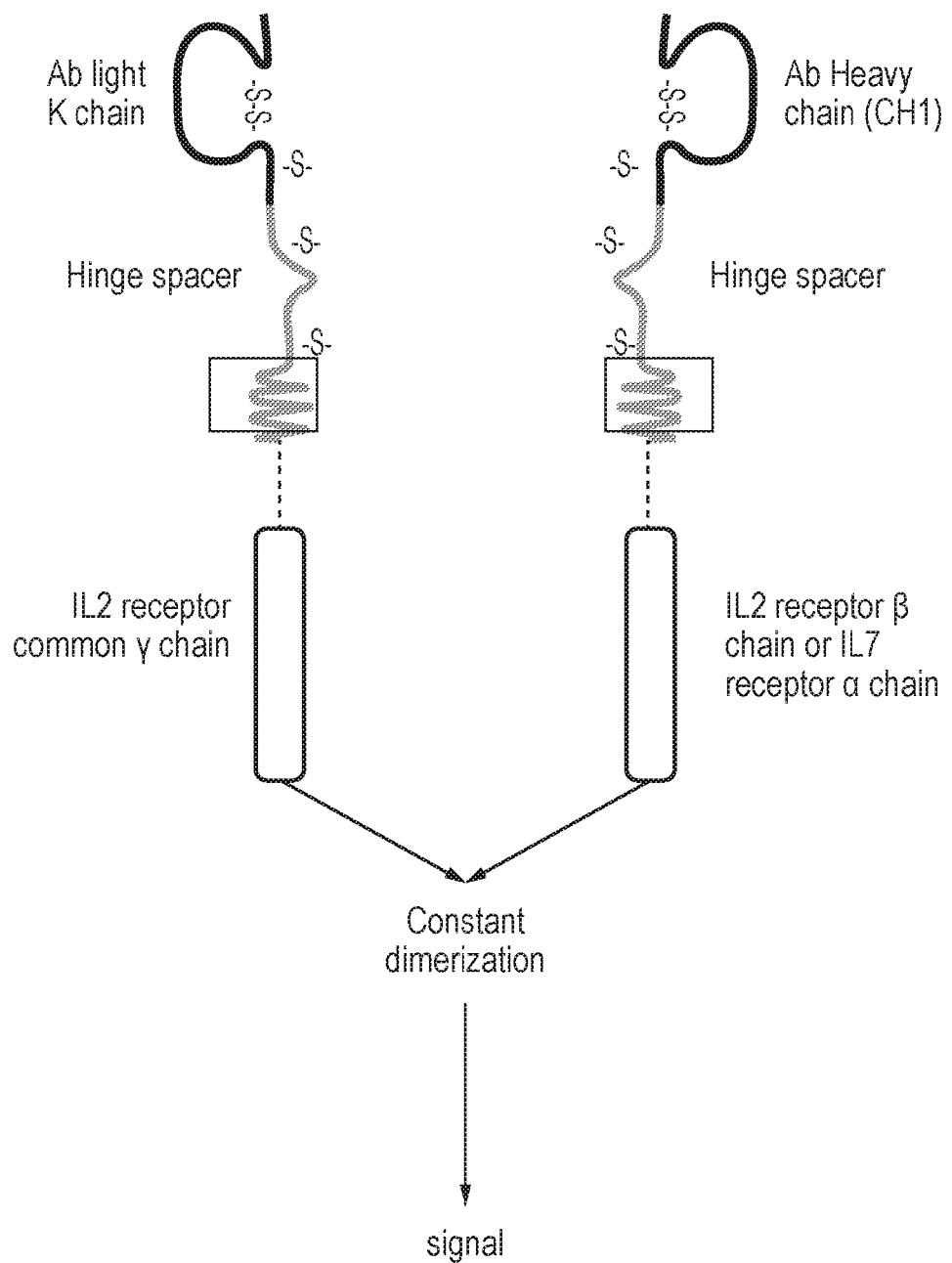
FIG. 2: Schematic diagram illustrating the constitutively active cytokine-signalling chimeric transmembrane protein described in WO2017/029512. The chimeric transmembrane protein comprises a dimerization domain and a cytokine receptor endodomain. The complex has a "Fab" type architecture, as the dimerization domain comprises antibody-type heavy and light chain constant regions. Constant dimerization between these domains brings together the IL2 receptor common γ chain with either the IL-2 receptor β chain or the IL-7 receptor αchain, leading to constitutive cytokine signalling.

The present inventors have developed a chimeric polypeptide which, when expressed in a cell, causes constitutive cytokine signalling. The polypeptide specifically binds to an endogenous cytokine receptor in the cell, causing cytokine signalling even in the absence of cytokine.

In a first aspect, the present invention provides a chimeric polypeptide comprising: an antigen-binding domain which constitutively binds to an ectodomain of a first chain of a cytokine receptor;
a transmembrane domain; and
an endodomain from a second chain of the cytokine receptor which chimeric polypeptide, when expressed in a cell, binds to the endogenous first chain of the cytokine receptor causing constitutive cytokine signalling.

In a first embodiment of the first aspect of the invention, the first chain of the cytokine receptor is a type I cytokine receptor γ-chain; and the second chain of the cytokine receptor is type I cytokine receptor α-chain or β-chain.

In a second embodiment of the first aspect of the invention, the first chain of the cytokine receptor is a type I cytokine receptor α-chain or β-chain; and the second chain of the cytokine receptor is type I cytokine receptor γ-chain.

The type I cytokine receptor α-chain or β-chain may be selected from one of the following: IL-2 receptor, IL-4 receptor, IL-7 receptor, IL-9 receptor, IL-13 receptor and IL-15 receptor.

The type I cytokine receptor α-chain or β-chain may be an IL-7 receptor α-chain.

The antigen binding domain may comprise a dAb or scFv which binds the ectodomain of the first chain of the cytokine receptor.

In a second aspect, the present invention provides a constitutively-active cytokine receptor which comprises a chimeric polypeptide according to the first aspect of the invention in association with the first chain of the cytokine receptor.

In a third aspect, the present invention provides a cell which comprises a constitutively-active cytokine receptor which comprises a chimeric polypeptide according to the first aspect of the invention in association with the endogenous first chain of the cytokine receptor.

The cell may also comprise a chimeric antigen receptor or an engineered T-cell receptor.

In a fourth aspect, the present invention provides a nucleic acid sequence encoding a chimeric polypeptide according to the first aspect of the invention.

In a fifth aspect, the present invention provides a nucleic acid construct which comprises a first nucleic acid sequence encoding a chimeric polypeptide according to the first aspect of the invention; and a second nucleic acid encoding a chimeric antigen receptor or an engineered T-cell receptor.

In a sixth aspect, there is provided a vector comprising a nucleic acid sequence according to the fourth aspect of the invention or a nucleic acid construct according to the fifth aspect of the invention.

In a seventh aspect, there is provided a method for making a cell according to the third aspect of the invention, which comprises the step of introducing: a nucleic acid sequence according to the fourth aspect of the invention; a nucleic acid construct according to the fifth aspect of the invention; or a vector according to the sixth aspect of the invention, into a cell.

In an eighth aspect, there is provided a method for inducing constitutive cytokine signalling in a cell, which comprises the step of expressing a chimeric polypeptide according to the first aspect of the invention in the cell.

In a ninth aspect, there is provided a method for blocking deleterious cytokine signalling in a cell, which comprises the step of expressing a chimeric polypeptide according to the first aspect of the invention in the cell, wherein the antigen binding domain constitutively binds to common gamma chain, and wherein one or more deleterious cytokine(s) signal(s) through a cytokine receptor which comprises common gamma chain.

In a tenth aspect, there is provided a pharmaceutical composition comprising a plurality of cells according to the third aspect of the invention.

In an eleventh aspect, there is provided a method for treating and/or preventing a disease, which comprises the step of administering a pharmaceutical composition according to the tenth aspect of the invention to a subject.

The method may comprise the following steps:
(i) isolation of a cell-containing sample from a subject;
(ii) transduction or transfection of the cells with: a nucleic acid sequence according to the fourth aspect of the invention; a nucleic acid construct according to the fifth aspect of the invention; or a vector according to the sixth aspect of the invention; and
(iii) administering the cells from (ii) to a the subject.

The disease may be a cancer.

In a twetfth aspect, there is provided a pharmaceutical composition according to the tenth aspect of the invention for use in treating and/or preventing a disease.

In a thirteenth aspect, there is provided the use of a cell according to the third aspect of the invention in the manufacture of a medicament for treating and/or preventing a disease.

A cytokine receptor which comprises a chimeric polypeptide of the present invention has an advantage over the "Fab"-type constitutively active molecules described in WO2017/029512 because only one recombinant polypeptide chain needs to be expressed in the cell. The cytokine receptor of the present invention makes use of an endogenous cytokine receptor in the cell in order to complete the constitutively active cytokine signalling complex.

The fact that the chimeric polypeptide of the present invention "hijacks" an endogenous cytokine receptor gives an additional advantage in that other, external, cytokine signals, which would normally signal through the endogenous receptor, will be at least partially blocked. This can be beneficial for the cell, as high levels of certain cytokines can be deleterious. For example high levels of IL-2 can cause T cells to differentiate into regulatory T cells.

Figure 3:
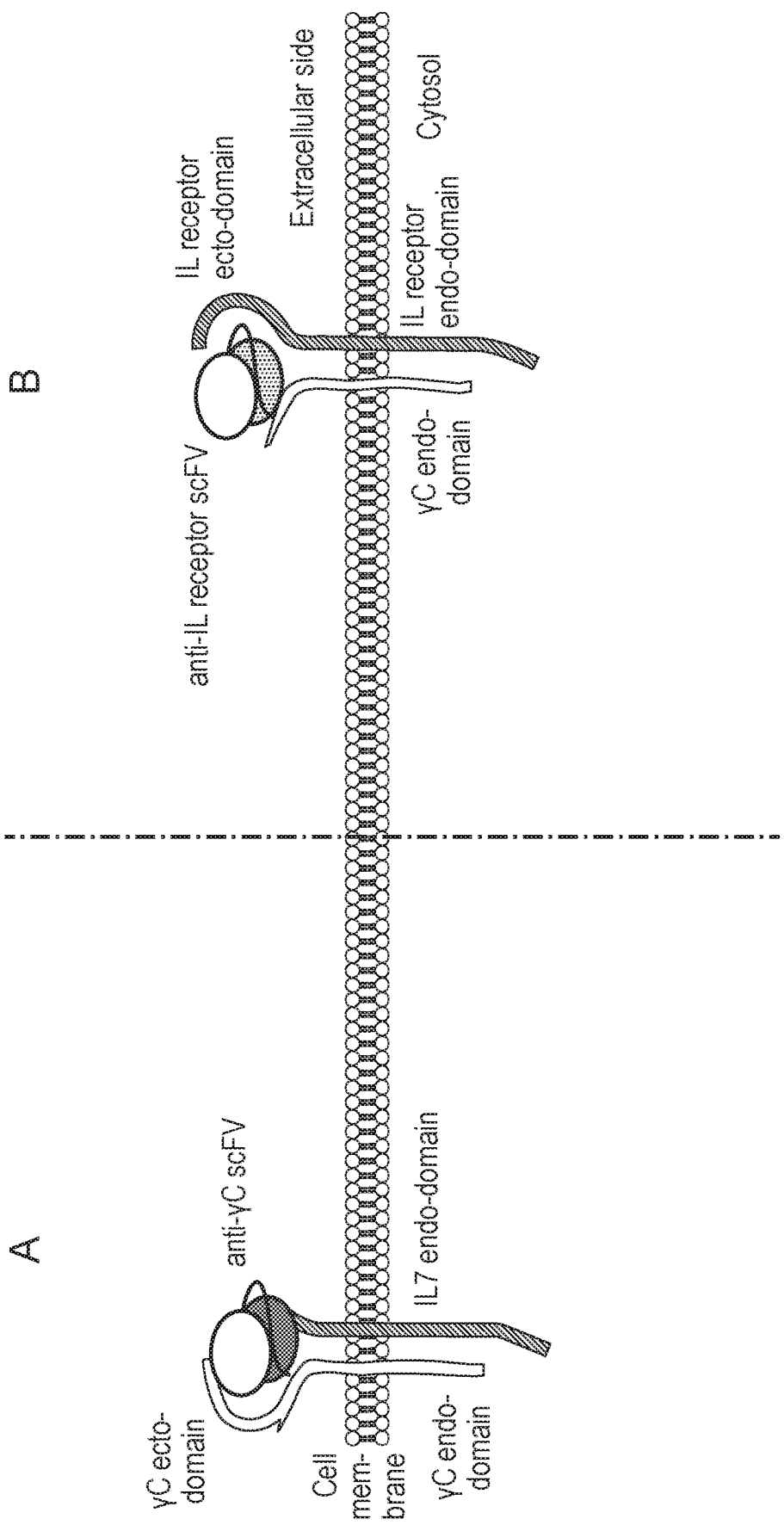
FIG. 3: Schematic diagram illustrating examples of constitutively active cytokine receptors of the invention. (A) The chimeric polypeptide comprises an anti-common gamma chain scFv ectodomain and an IL-7 endodomain. When expressed inside a cell, binding of the anti-γC scFv to engogenous gamma chain produces a constitutively active cytokine receptor. In this arrangement the cell receives only one type of cytokine signal, for example, IL-7; (B) The chimeric polypeptide comprises an anti-IL-receptor scFv ectodomain and an γC endodomain. When expressed inside a cell, binding of the anti-ILR scFv to an engogenous IL-receptor chain produces a constitutively active cytokine receptor. In this arrangement the cell receives may receive multiple cytokine signals, all of which signal through γC. The cytokine signal is regulated by physiological expression of cytokine receptor.

The arrangement shown in FIG. 3a, which comprises an anti-γC scFv ectodomain, has the additional advantage that the cell is not engineered to encode common gamma chain. Retroviral expression of the common gamma chain has previously been associated with leukaemiagenesis in X-SCID patients.

The arrangement shown in FIG. 3a avoids over-expression the common gamma chain. Unlike the Fab-type system, where the cell comprises both with wild type gamma chain and the transgenic gamma chain, in the system shown in FIG. 3a, only the wild-type gamma chain is expressed in the cell. As the gamma chain is expressed physiologically by the cell it is naturally upregulated and down-regulated as needed.

DETAILED DESCRIPTION

Chimeric Polypeptide

A chimeric polypeptide is a molecule which comprises (i) an antigen-binding domain which constitutively binds to an ectodomain of a first chain of a cytokine receptor; and (ii) an endodomain from a second chain of the cytokine receptor Cytokine Receptors and Signalling Many cell functions are regulated by members of the cytokine receptor superfamily. Signalling by these receptors depends upon their association with Janus kinases (JAKs), which couple ligand binding to tyrosine phosphorylation of signalling proteins recruited to the receptor complex. Among these are the signal transducers and activators of transcription (STATs), a family of transcription factors that contribute to the diversity of cytokine responses.

When a cytokine receptor binds its ligand, one or more of the following intracellular signalling pathways may be initiated:
(i) the JAK-STAT pathway;
(ii) the MAP kinase pathway; and
(iii) the Phosphoinositide 3-kinase (PI3K) pathway.

The same pathways may be initiated by the constitutively active cytokine receptor of the present invention.

The JAK-STAT system consists of three main components: (1) a receptor (2) Janus kinase (JAK) and (3) Signal Transducer and Activator of Transcription (STAT).

JAKs, which have tyrosine kinase activity, bind to cell surface cytokine receptors. The binding of the ligand to the receptor triggers activation of JAKs. With increased kinase activity, they phosphorylate tyrosine residues on the receptor and create sites for interaction with proteins that contain phosphotyrosine-binding SH2 domains. STATs possessing SH2 domains capable of binding these phosphotyrosine residues are recruited to the receptors, and are themselves tyrosine-phosphorylated by JAKs. These phosphotyrosines then act as binding sites for SH2 domains of other STATs, mediating their dimerization. Different STATs form hetero- or homodimers. Activated STAT dimers accumulate in the cell nucleus and activate transcription of their target genes.

Cytokine Receptor Endodomain

The chimeric polypeptide of the present invention comprises an endodomain which causes "cytokine-type" cell signalling when in the presence of an endogenous cytokine receptor chain.

The endodomain may be a cytokine receptor endodomain.

The endodomain may be derived from a type I cytokine receptor. Type I cytokine receptors share a common amino acid motif (WSxWS) in the extracellular portion adjacent to the cell membrane.

The endodomain may be derived from a type II cytokine receptor. Type II cytokine receptors include those that bind type I and type II interferons, and those that bind members of the interleukin-10 family (interleukin-10, interleukin-20 and interleukin-22).

Type I cytokine receptors include:
(i) Interleukin receptors, such as the receptors for IL-2, IL-3, IL-4, IL-5, IL-6, IL-7, IL-9, IL-11, IL-12, IL13, IL-15, IL-21, IL-23 and IL-27;
(ii) Colony stimulating factor receptors, such as the receptors for erythropoietin, GM-CSF, and G-CSF; and
(iii) Hormone receptor/neuropeptide receptor, such as hormone receptor and prolactin receptor Members of the type I cytokine receptor family comprise different chains, some of which are involved in ligand/cytokine interaction and others that are involved in signal transduction. For example the IL-2 receptor comprises an α-chain, a β-chain and a γ-chain.

The IL-2 receptor common gamma chain (also known as CD132) is shared between the IL-2 receptor, IL-4 receptor, IL-7 receptor, IL-9 receptor, IL-13 receptor and IL-15 receptor.

IL-2

IL-2 binds to the IL-2 receptor, which has three forms, generated by different combinations of three different proteins, often referred to as "chains": α, β and γ; these subunits are also parts of receptors for other cytokines. The β and γchains of the IL-2R are members of the type I cytokine receptor family.

The three receptor chains are expressed separately and differently on various cell types and can assemble in different combinations and orders to generate low, intermediate, and high affinity IL-2 receptors.

The αchain binds IL-2 with low affinity, the combination of β and γ together form a complex that binds IL-2 with intermediate affinity, primarily on memory T cells and NK cells; and all three receptor chains form a complex that binds IL-2 with high affinity (Kd~10-11 M) on activated T cells and regulatory T cells.

The three IL-2 receptor chains span the cell membrane and extend into the cell, thereby delivering biochemical signals to the cell interior. The alpha chain does not participate in signalling, but the beta chain is complexed with the tyrosine phosphatase JAK1. Similarly the gamma chain complexes with another tyrosine kinase called JAK3. These enzymes are activated by IL-2 binding to the external domains of the IL-2R.

IL-2 signalling promotes the differentiation of T cells into effector T cells and into memory T cells when the initial T cells are also stimulated by an antigen. Through their role in the development of T cell immunologic memory, which depends upon the expansion of the number and function of antigen-selected T cell clones, they also have a key role in long-term cell-mediated immunity.

The chimeric polypeptide of the present invention may comprise an endodomain from the IL-2 receptor β-chain or the IL-2 receptor (i.e. common) γ-chain The amino acid sequences for the endodomains of the IL-2 β-chain and common γ-chain are shown as SEQ ID No. 1 and 2

```
SEQ ID No. 1: Endodomain derived from human
common gamma chain:
ERTMPRIPTLKNLEDLVTEYHGNFSAWSGVSKGLAESLQPDYSERLCLVS

EIPPKGGALGEGPGASPCNQHSPYWAPPCYTLKPET

SEQ ID No. 2: Endodomain derived from human
IL-2Rβ:
NCRNTGPWLKKVLKCNTPDPSKFFSQLSSEHGGDVQKWLSSPFPSSSFSP

GGLAPEISPLEVLERDKVTQLLLQQDKVPEPASLSSNHSLTSCFTNQGYF

FFHLPDALEIEACQVYFTYDPYSEEDPDEGVAGAPTGSSPQPLQPLSGED

DAYCTFPSRDDLLLFSPSLLGGPSPPSTAPGGSGAGEERMPPSLQERVPR

DWDPQPLGPPTPGVPDLVDFQPPPELVLREAGEEVPDAGPREGVSFPWSR

PPGQGEFRALNARLPLNTDAYLSLQELQGQDPTHLV
```

The term "derived from" means that the endodomain of the chimeric polypeptide of the invention has the same sequence as the wild-type sequence of the endogenous molecule, or a variant thereof which retains the ability to form a complex with JAK-1 or JAK-3 and activate one of the signalling pathways mentioned above.

A "variant" sequence having at least 80, 85, 90, 95, 98 or 99% sequence identity to the wild-type sequence (e.g. SEQ ID Nos. 1 or 2), providing that the variant sequence retains the function of the wild-type sequence i.e. the ability to form a complex with JAK-1 or JAK-3 and activate, for example, the JAK-STAT signalling pathway.

The percentage identity between two polypeptide sequences may be readily determined by programs such as BLAST which is freely available at http://blast.ncbi.nlm.nih.gov

IL-7

The interleukin-7 receptor is made up of two chains: the interleukin-7 receptor-αchain (CD127) and common-γchain receptor (CD132). The common-γchain receptors is shared with various cytokines, including interleukin-2, -4, -9, and -15. Interleukin-7 receptor is expressed on various cell types, including naive and memory T cells.

The interleukin-7 receptor plays a critical role in the development of lymphocytes, especially in V(D)J recombination. IL-7R also controls the accessibility of a region of the genome that contains the T-cell receptor gamma gene, by STAT5 and histone acetylation. Knockout studies in mice suggest that blocking apoptosis is an essential function of this protein during differentiation and activation of T lymphocytes.

The chimeric polypeptide of the present invention may comprise an endodomain from the IL-7 receptor α-chain and/or the IL-7 receptor (i.e. common) γ-chain, or a variant thereof.

The amino acid sequence for the endodomain of the IL-7 α-chain is shown as SEQ ID No. 3.

```
Endodomain derived from human IL-7Rα:
                                      SEQ ID No. 3
KKRIKPIVWPSLPDHKKTLEHLCKKPRKNLNVSFNPESFLDCQIHRVDDI

QARDEVEGFLQDTFPQQLEESEKQRLGGDVQSPNCPSEDVVITPESFGRD

SSLTCLAGNVSACDAPILSSSRSLDCRESGKNGPHVYQDLLLSLGTTNST

LPPPFSLQSGILTLNPVAQGQPILTSLGSNQEEAYVTMSSFYQNQ
```

IL-15

Interleukin 15 (IL-15) is a cytokine with structural similarity to IL-2. Like IL-2, IL-15 binds to and signals through a complex composed of IL-2/IL-15 receptor beta chain (CD122) and the common gamma chain (gamma-C, CD132). IL-15 is secreted by mononuclear phagocytes (and some other cells) following viral infection. IL-15 induces cell proliferation of natural killer cells.

Interleukin-15 receptor consists of an interleukin 15 receptor alpha subunit and shares common beta and gamma subunits with the IL-2 receptor.

Spacer

The chimeric polypeptide of the present invention may comprise a spacer to connect the antigen-binding domain with the transmembrane domain and spatially separate the antigen-binding domain from the endodomain. A flexible spacer allows to the antigen-binding domain to orient in different directions to enable antigen binding.

The spacer should be of an appropriate length so that the antigen-binding domain of the chimeric polypeptide is positioned at an appropriate distance from the cell membrane to specifically bind the endogenous cytokine receptor chain.

Where the cell of the present invention comprises a chimeric polypeptide and a chimeric antigen receptor (CAR), the spacer of the chimeric polypeptide and the CAR may be different, for example, having a different length. The spacer of the CAR may be longer than the spacer of the chimeric polypeptide.

The spacer sequence may, for example, comprise an IgG1 Fc region, an IgG1 hinge or a CD8 stalk or an alternative sequence which has similar length and/or domain spacing properties.

A human IgG1 spacer may be altered to remove Fc binding motifs.

Examples of amino acid sequences for these spacers are given below:

```
(hinge-CH2CH3 of human IgG1)
                                      SEQ ID No. 4
AEPKSPDKTHTCPPCPAPPVAGPSVFLFPPKPKDTLMIARTPEVTCVVVD

VSHEDPEVKFNVVYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGKKD (human CD8 stalk):
                                      SEQ ID No. 5
TTTPAPRPPTPAPTIASQPLSLRPEACRPAAGGAVHTRGLDFACDI (human IgG1 hinge):
                                      SEQ ID No. 6
AEPKSPDKTHTCPPCPKDPK
```

TRANSMEMBRANE DOMAIN

The transmembrane domain is the sequence of a chimeric polypeptide that spans the membrane. It may comprise a hydrophobic alpha helix. The transmembrane domain may be derived from CD28, which gives good receptor stability.

Alternatively the transmembrane domain may be derived from a cytokine receptor, for example the same cytokine from which the endodomain is derived.

The transmembrane domain may, for example be derived from IL-2R, IL-7R or IL-15R.

```
Transmembrane derived from human common
gamma chain:
                                      SEQ ID No. 7
VVISVGSMGLIISLLCVYFWL Transmembrane derived from human IL-2Rβ:
                                      SEQ ID No. 8
IPWLGHLLVGLSGAFGFIILVYLLI Transmembrane derived from human IL-7Rα:
                                      SEQ ID No. 9
PILLTISILSFFSVALLVILACVLW Transmembrane derived from human IL-15Rα:
                                      SEQ ID No. 10
AISTSTVLLCGLSAVSLLACYL
```

Antigen-Binding Domain

The antigen-binding domain of the chimeric polypeptide of the present invention specifically binds to an ectodomain of a cytokine receptor. It may bind to the common gamma chain, or to an α- or β-chain, for example the IL-7αchain.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; the binding domain from a natural receptor for the target antigen; a peptide with sufficient affinity for the target ligand; a single domain binder such as a camelid; an artificial binder single as a Darpin; or a single-chain derived from a T-cell receptor.

Suitable antibodies from which antigen-binding domains may be derived, are known in the art. For example, U.S. Pat. No. 6,323,027, which is incorporated by reference, describes antibodies which specifically bind to the common γ-chain.

The antigen binding domain may comprise an scFv which binds to the common γ-chain. The antigen binding domain may comprise the light chain CDRs shown as SEQ ID No. 11-13 and/or the heavy chain CDRs shown as SEQ ID No. 14-16.

```
(CDRL1):
                                    SEQ ID No. 11
KASQDVTTAVA (CDRL2):
                                    SEQ ID No. 12
WASTRHT (CDRL3):
                                    SEQ ID No. 13
QQHITPVVT (CDRH1):
                                    SEQ ID No. 14
SYGVH (CDRH2):
                                    SEQ ID No. 15
VIWAGGSTBYNSALM (CDRH3):
                                    SEQ ID No. 16
EGSTVDSMDY
```

The antigen binding domain may comprise the VL domain shown as SEQ ID No. 17 and/or the VH domain shown as SEQ ID No. 18.

```
(VL):
                                    SEQ ID No. 17
DIVMTQSHKFMSTSVGDSITITCKASQDVTTAVAWYQQKPGQSPKLLIYW

ASTRHTGVPDRFTGSGSGTDYTLTISSVQAEDLALYYCQQHYITPVVTFG

GGTKLEI (VH):
                                    SEQ ID No. 18
LQESGPGLVAPQSQSLSITCTVDGFSLTSYGVHWVRQPPGKGLEWLGVIW

AGGSTNYNSALMSRLNINRDNSKSQIFLKMNSLQTDDTAIYYCAREGSTV

DSMDYWGQGTTVT
```

Chimeric Antigen Receptors (CAR)

The cell of the present invention may also comprise one or more chimeric antigen receptor(s). The CAR(s) may be specific for a tumour-associated antigen.

Classical CARs are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like or ligand-based antigen binding site. A trans-membrane domain anchors the protein in the cell membrane and connects the spacer to the endodomain.

Early CAR designs had endodomains derived from the intracellular parts of either the γchain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

The cell of the present invention may comprise one or more CAR(s).

The CAR(s) may comprise an antigen-binding domain, a spacer domain, a transmembrane domain and an endodomain. The endodomain may comprise or associate with a domain which transmit T-cell activation signals.

Signal Peptide

The chimeric polypeptide and/or CAR may comprise a signal peptide so that when it/they is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the sequence shown as SEQ ID No. 19, 20 or 21 or a variant thereof having 5, 4, 3, 2 or 1 amino acid mutations (insertions, substitutions or additions) provided that the signal peptide still functions to cause cell surface expression of the CAR.

```
SEQ ID No. 19: MGTSLLCWMALCLLGADHADG
```

The signal peptide of SEQ ID No. 19 is compact and highly efficient and is derived from TCR beta chain. It is predicted to give about 95% cleavage after the terminal glycine, giving efficient removal by signal peptidase.

```
SEQ ID No. 20: MSLPVTALLLPLALLLHAARP
```

The signal peptide of SEQ ID No. 20 is derived from IgG1.

```
SEQ ID No. 21: MAVPTQVLGLLLLWLTDARC
```

The signal peptide of SEQ ID No. 21 is derived from CD8a.

Car Endodomain

The endodomain is the portion of a classical CAR which is located on the intracellular side of the membrane.

The endodomain is the signal-transmission portion of a classical CAR. After antigen recognition by the antigen binding domain, individual CAR molecules cluster, native CD45 and CD148 are excluded from the synapse and a signal is transmitted to the cell.

The CAR endodomain may be or comprise an intracellular signalling domain. In an alternative embodiment, the endodomain of the present CAR may be capable of interacting with an intracellular signalling molecule which is present in the cytoplasm, leading to signalling.

The intracellular signalling domain or separate intracellular signalling molecule may be or comprise a T cell signalling domain.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together.

Nucleic Acid

The present invention also provides a nucleic acid encoding a chimeric polypeptide of the invention.

The nucleic acid may have the structure:
AgB-spacer-TM-endo
in which
AgB1 is a nucleic acid sequence encoding the antigen-binding domain of the chimeric polypeptide;
spacer 1 is a nucleic acid sequence encoding the spacer of the chimeric polypeptide; TM1 is a a nucleic acid sequence encoding the transmembrane domain of the chimeric polypeptide;
endo 1 is a nucleic acid sequence encoding the endodomain of the chimeric polypeptide.

Nucleic Acid Construct

The present invention also provides a nucleic acid construct encoding a chimeric polypeptide of the invention and a CAR. Such a construct may have the structure:
CPAgB-CPspacer-CPTM-CPendo-coexpr-CARAgB-CAR-spacer-CARTM-CARendo or
CARAgB-CARspacer-CARTM-CARendo-coexpr-CPAgB-CPspacer-CPTM-CPendo
in which
CPAgB is a nucleic acid sequence encoding the antigen-binding domain of the chimeric polypeptide;
CPspacer is a nucleic acid sequence encoding the spacer of the chimeric polypeptide;
CPTM is a a nucleic acid sequence encoding the transmembrane domain of the chimeric polypeptide;
CPendo is a nucleic acid sequence encoding the endodomain of the chimeric polypeptide;
coexpr is a nucleic acid sequence enabling co-expression of both the chimeric polypeptide and the CAR
CARAgB is a nucleic acid sequence encoding the antigen-binding domain of the CAR;
CARspacer is a nucleic acid sequence encoding the spacer of the CAR; CARTM is a nucleic acid sequence encoding the transmembrane domain of the CAR; and
CARendo is a nucleic acid sequence encoding the endodomain of the CAR.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

In the structure above, "coexpr" is a nucleic acid sequence enabling co-expression of both first and second CARs. It may be a sequence encoding a cleavage site, such that the nucleic acid construct produces a chimeric polypeptide and a CAR, joined by a cleavage site(s). The cleavage site may be self-cleaving, such that when the polypeptide is produced, it is immediately cleaved into individual peptides without the need for any external cleavage activity.

The cleavage site may be any sequence which enables the chimeric polypeptide and CAR to become separated.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may, for example be a furin cleavage site, a Tobacco Etch Virus (TEV) cleavage site or encode a self-cleaving peptide.

A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above).

The cleavage site may comprise the 2A-like sequence shown as SEQ ID No. 22 (RAEGRGSLLTCGDVEENPGP).

The present invention also provides a kit comprising a chimeric polypeptide according to the invention and one or more CAR(s) or TCR(s).

Engineered T-Cell Receptor (TCR)

The cell of the present invention may express a T-cell receptor (TCR), for example an engineered or non-endogenous TCR.

The TCR is a molecule found on the surface of T cells which is responsible for recognizing fragments of antigen as peptides bound to major histocompatibility complex (MHC) molecules.

The TCR is a heterodimer composed of two different protein chains. In humans, in 95% of T cells the TCR consists of an alpha (α) chain and a beta (β) chain (encoded by TRA and TRB, respectively), whereas in 5% of T cells the TCR consists of gamma and delta (γ/δ) chains (encoded by TRG and TRD, respectively).

When the TCR engages with antigenic peptide and MHC (peptide/MHC), the T lymphocyte is activated through signal transduction.

In contrast to conventional antibody-directed target antigens, antigens recognized by the TCR can include the entire array of potential intracellular proteins, which are processed and delivered to the cell surface as a peptide/MHC complex.

It is possible to engineer cells to express heterologous (i.e. non-native) TCR molecules by artificially introducing the TRA and TRB genes; or TRG and TRD genes into the cell using vector. For example the genes for engineered TCRs may be reintroduced into autologous T cells and transferred back into patients for T cell adoptive therapies.

The present invention also provides a cell which comprises a TCR and a chimeric polypeptide according to the first aspect of the invention.

Vector

The present invention also provides a vector, or kit of vectors, which comprises one or more nucleic acid sequence(s) encoding a chimeric polypeptide according to the first aspect of the invention and optionally one or more CAR(s) or TCR(s). Such a vector may be used to introduce the nucleic acid sequence(s) into a host cell so that it expresses a chimeric polypeptide according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cytokine Receptor

There is also provided a constitutively-active cytokine receptor which comprises a chimeric polypeptide of the invention in association with a cytokine receptor chain.

The chimeric polypeptide may associate with the first chain of a cytokine receptor. It may bind the ectodomain of the cytokine receptor chain via its antigen binding domain. The cytokine receptor chain which binds the chimeric polypeptide may be endogenous i.e. a polypeptide which is naturally encoded by the cell.

Cell

The present invention provides a cell which comprises a chimeric polypeptide of the invention and optionally one of more CAR(s) or TCR(s).

The cell may comprise a nucleic acid or a vector of the present invention.

The cell may comprise a constitutively active cytokine receptor as defined above.

The cell may be a cytolytic immune cell such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described–naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The chimeric polypeptide-expressing cells of the invention may be any of the cell types mentioned above.

T or NK cells according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, chimeric polypeptide-expressing cells are generated by introducing DNA or RNA coding for the chimeric polypeptide by one of many means including transduction with a viral vector, transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the chimeric polypeptide according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding a chimeric polypeptide.

The T or NK cells may then by purified, for example, selected on the basis of expression of the antigen-binding domain of the antigen-binding polypeptide.

Inducing/Blocking Cytokine Signalling

The present invention provides a method for inducing constitutive cytokine signalling in a cell, which comprises the step of expressing a chimeric polypeptide as defined above in the cell. The chimeric polypeptide binds to an endogenous cytokine receptor chain via the antigen binding domain, forming a constitutively active cytokine receptor at the cell surface.

The present invention also provides a method for blocking deleterious cytokine signalling in a cell, by expressing a chimeric polypeptide of the invention in the cell. The chimeric polypeptide binds to a cytokine receptor chain, preventing that chain pairing with other endogenous cytokine receptor partner chains. For example, where the, wherein the antigen binding domain constitutively binds to common gamma chain, it may reduce the concentration of one or more of the following receptors at the cell surface: IL-2 receptor, IL-4 receptor, IL-7 receptor, IL-9 receptor, IL-13 receptor and IL-15.

This may block deleterious cytokine signalling in the cell, for example excessive IL-2 mediated signalling.

Pharmaceutical Composition

The present invention also relates to a pharmaceutical composition containing a plurality of cells according to the invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The T or NK cell-containing sample may be isolated from a subject or from other sources, for example as described above. The T or NK cells may be isolated from a subject's own peripheral blood (1st party), or in the setting of a haematopoietic stem cell transplant from donor peripheral blood (2nd party), or peripheral blood from an unconnected donor (3rd party).

The present invention provides a chimeric polypeptide-expressing cell of the present invention for use in treating and/or preventing a disease.

The invention also relates to the use of a chimeric polypeptide-expressing cell of the present invention in the manufacture of a medicament for the treatment and/or prevention of a disease.

The disease to be treated and/or prevented by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The cells of the present invention may be capable of killing target cells, such as cancer cells. The target cell may be characterised by the presence of a tumour secreted ligand or chemokine ligand in the vicinity of the target cell. The target cell may be characterised by the presence of a soluble ligand together with the expression of a tumour-associated antigen (TAA) at the target cell surface.

The cells and pharmaceutical compositions of present invention may be for use in the treatment and/or prevention of the diseases described above.

The cells and pharmaceutical compositions of present invention may be for use in any of the methods described above.

The invention will now be further described by way of Examples, which are meant to serve to assist one of ordinary

EXAMPLES

Figure 4:
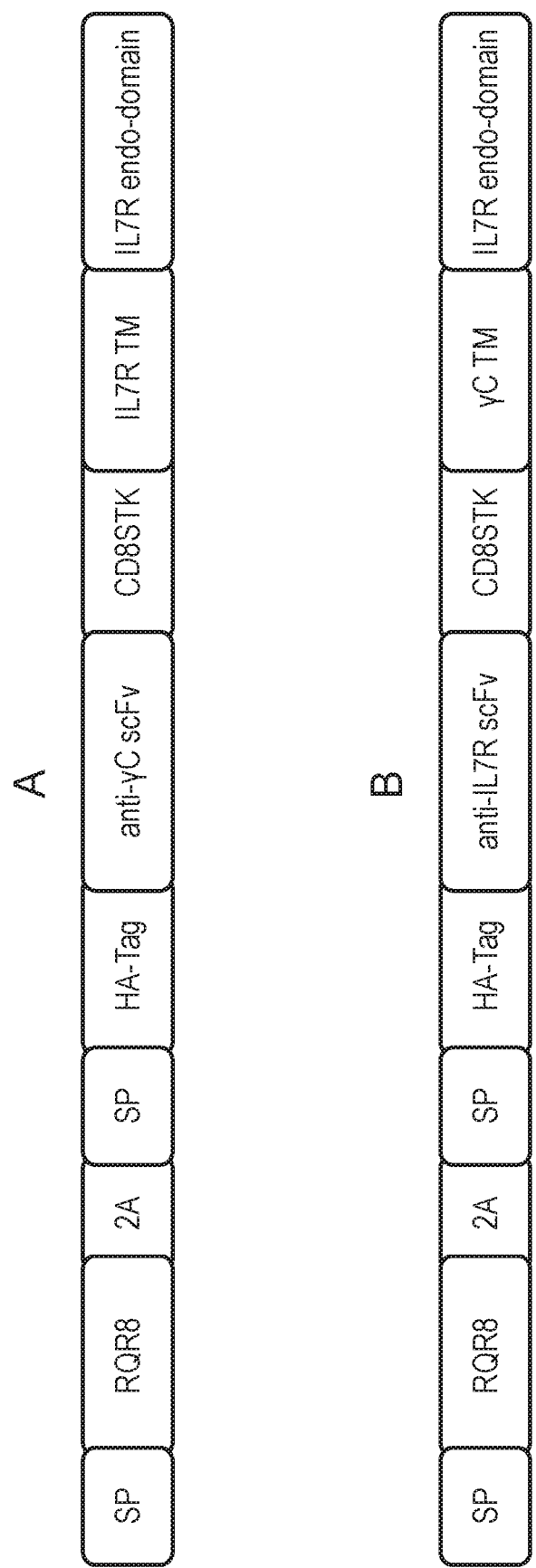
FIG. 4: Construct diagrams for the two chimeric polypeptides made and tested in Example 1. (A) The construct coexpresses a marker gene (RQR8) and a chimeric polypeptide comprising an anti-γC scFv ectodomain and an IL-7 receptor endodomain. (B) The construct coexpresses a marker gene (RQR8) and a chimeric polypeptide comprising an anti-IL-7 receptor scFv ectodomain and a γC endodomain. "SP"—signal peptide; "RQR8"—the sort-suicide gene RQR8; "2A"—a FNDV derived 2A peptide cleavage site; "HA-Tag"—hemagglutinin tag; anti-γC/anti-IL7R scFv-scFv which specifically binds γC/IL7 receptor; "CD8STK"—spacer sequence from human CD8 stalk; "IL7R/γC" TM—transmembrane domain from IL7 receptor/gamma chain; "IL7R/γC endodomain"—endodomain from IL7 receptor or gamma chain.

Example 1—Design and Testing of Two Chimeric Polypeptides Giving Constitutively Active Cytokine-Signalling Two chimeric polypeptides were designed and tested using the constructs illustrated in FIG. 4. The first construct encodes a chimeric polypeptide comprising an anti-γC scFv ectodomain and an IL-7 receptor endodomain. The second construct encodes a chimeric polypeptide comprising an anti-IL-7 receptor scFv ectodomain and a γC endodomain.

A nucleic acid encoding a marker (RQR8) is cloned in-frame with a nucleic acid sequences encoding one of these two polypeptides separated by a 2A-peptide encoding sequence.

The murine cell line 2E8 (ATCC TIB-239™) is dependent on IL7 for cell growth. In the absence of an IL-7 signal the cells undergo apoptosis. 2E8 cells are transduced with a vector expressing the chimeric polypeptides described above, together with RQR8, or left untransduced (WT). As a positive control, cells of all three types are co-cultured with 100 U/ml murine IL7. Cell proliferation is assessed after 3 and 7 days of culture.

The amino acid sequences for the two constructs tested are shown below.

Amino Acid Sequence of the Components of the Construct Shown in FIG. 4A

```
Signal Sequence from Murine heavy chain
                                        SEQ ID No. 23
MGWSCIILFLVATATGVHS RQR8
                                        SEQ ID No. 24
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDIYIWAPLAGTCGVLLLSLVITLYCNHRNRRRVC

KCPRPVVRA

2A
                                        SEQ ID No. 25
EGRGSLLTCGDVEENPG

Signal sequence from mouse kappa chain
                                        SEQ ID No. 26
METDTLILVVVLLLLVPGSTG anti-γC Light Chain variable region
                                        SEQ ID No. 27
DIVMTQSHKFMSTSVGDSITITCKASQDVTTAVVYQQKPGQSPKWYWA

STRHTGVPDRFTGSGSGTDYTLTISSVQAEDLALYYCQQHYITPVVTFGG

GTKLEIKR

Linker
                                        SEQ ID No. 28
SGGGGSGGGGSGGGGS anti-γC Heavy Chain Variable Region
                                        SEQ ID No. 29
QVQLQESGPGLVAPQSQSLSITCTVDGFSLTSYGVHVVVRQPPGKGLEWL

GVIWAGGSTNYNSALMSRLNINRDNSKSQ1FLKMNSLQTDDTAIYYCARE

GSTVDSMDYWGQGTTVTVSS

IL7Ra transmembrane region
                                        SEQ ID No. 9
PILLTISILSFFSVALLVILACVLW IL7Ra endodomain
                                        SEQ ID No. 3
KKRIKPIVWPSLPDHKKTLEHLCKKPRKNLNVSFNPESFLDCQIHRVDDI

QARDEVEGFLQDTFPQQLEESEKQRLGGDVQSPNCPSEDVVITPESFGRD

SSLTCLAGNVSACDAPILSSSRSLDCRESGKNGPHVYQDLLLSLGTTNST

LPPPFSLQSGILTLNPVAQGQPILTSLGSNQEEAYVTMSSFYQNQ
```

Amino Acid Sequence of the Components of the Construct Shown in FIG. 4B

```
Signal Sequence from Murine heavy chain
                                        SEQ ID No. 23
MGWSCIILFLVATATGVHS RQR8
                                        SEQ ID No. 24
MGTSLLCWMALCLLGADHADACPYSNPSLCSGGGGSELPTQGTFSNVSTN

VSPAKPTTTACPYSNPSLCSGGGGSPAPRPPTPAPTIASQPLSLRPEACR

PAAGGAVHTRGLDFACDIYIWAPLAGTCGVLLLSLVITLYCNHRNRRRVC

KCPRPVVRA

2A
                                        SEQ ID No. 25
EGRGSLLTCGDVEENPG

Signal sequence from mouse kappa chain
                                        SEQ ID No. 26
METDTLILVVVLLLLVPGSTG HA tag
                                        SEQ ID No. 30
YPYDVPDYA anti-IL2receptor beta (CD122) specific variable light chain
                                        SEQ ID No. 31
MDFQVQIFSFLLISASVISRGQWLTQSPVIMSASPGEKVTMTCSAISSSY

MYVVYQQKPGSSPRLLIYDTSNLVSGVPVRFSGSGSGTSYSLTISRMEAE

DAATYYCQQWNTYPYTFGGGTKLE1K

Linker
                                        SEQ ID No. 28
SGGGGSGGGGSGGGGS anti-IL2receptor beta (CD122) specific variable heavy chain
                                        SEQ ID No. 32
MKLWLNWVFLLTLLHGIQCEVKLVESGGGLVQPGGSLRLSCATSGFTFSD

FYMEWVRQPPGKRLEWIAASRNKANDYTTEYSASVKGRFIVSRDTSQSIL

YLQMNALRAEDTAIYYCARSYYRYDGMDYVVGQGTSVTVSS

CD8stalk
                                        SEQ ID No. 5
TTTPAPRPPTPAPTIASQPLSLRPEACRPAAGGAVHTRGLDFACDI IL2R common gamma chain TM
                                        SEQ ID No. 7
VVISVGSMGLIISLLCVYFWL IL2R common gamma chain endodomain
                                        SEQ ID No. 1
ERTMPRIPTLKNLEDLVTEYHGNFSAWSGVSKGLAESLQPDYSERLCLVS

EIPPKGGALGEGPGASPCNQHSPYWAPPCYTLKPET
```

Example 2—In Vitro Testing

T-cells are transduced with either a CAR, or a construct which co-expresses a CAR with a chimeric polypeptide. Transduced T-cells are cultured in the presence or absence of exogenous IL2 and at different effector to target ratios. Proliferation of T-cells and killing of target cells is determined. In this way, the contribution the chimeric polypeptide makes to proliferation and survival of T-cells can be measured.

Example 3—In Vivo Testing

T-cells transduced with either a CAR, or a construct which co-expresses a CAR with a chimeric polypeptide are administered to tumour-bearing NSG mice. Mice within each cohort are sacrificed at different time-points and engraftment/expansion of T-cells at the tumour bed or within lymphoid tissues such as lymph nodes, spleen and bone-marrow measured by flow cytometry of said tissues.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A chimeric polypeptide comprising:
   an antigen-binding domain that constitutively binds to an ectodomain of a first chain of a cytokine receptor;
   a transmembrane domain; and
   an endodomain from a second chain of the cytokine receptor;
   wherein the chimeric polypeptide, when expressed in a cell that expresses the cytokine receptor, binds to an endogenous first chain of the cytokine receptor expressed in the cell, causing constitutive cytokine signalling in the cell.

2. A chimeric polypeptide according to claim 1, wherein:

the first chain of the cytokine receptor is a type I cytokine receptor γ-chain and the second chain of the cytokine receptor is type I cytokine receptor α-chain or β-chain, or the first chain of the cytokine receptor is a type I cytokine receptor α-chain or β-chain, and the second chain of the cytokine receptor is type I cytokine receptor γ-chain.

3. A chimeric polypeptide according to claim 2, wherein the type I cytokine receptor α-chain or β-chain is from IL-2 receptor, IL-4 receptor, IL-7 receptor, IL-9 receptor, IL-13 receptor or IL-15 receptor.

4. A chimeric polypeptide according to claim 3, wherein the type I cytokine receptor α-chain or β-chain is IL-7 receptor α-chain.

5. A chimeric polypeptide according to claim 1, wherein the antigen-binding domain comprises a dAb or scFv that binds the ectodomain of the first chain of the cytokine receptor.

6. A constitutively-active cytokine receptor which comprises a chimeric polypeptide according to any preceding claim 1 in association with the first chain of the cytokine receptor.

7. A cell which comprises a constitutively-active cytokine receptor which comprises a chimeric polypeptide according to claim 1 in association with the endogenous first chain of the cytokine receptor.

8. A cell according to claim 7, which also comprises a chimeric antigen receptor or an engineered T-cell receptor.

9. A nucleic acid comprising a nucleotide sequence encoding a chimeric polypeptide, the chimeric polypeptide comprising:

an antigen-binding domain that constitutively binds to an ectodomain of a first chain of a cytokine receptor;

a transmembrane domain; and an endodomain from a second chain of the cytokine receptor;

wherein the chimeric polypeptide, when expressed in a cell that expresses the cytokine receptor, binds to an endogenous first chain of the cytokine receptor expressed in the cell, causing constitutive cytokine signaling in the cell.

10. A nucleic acid construct which comprises a first nucleic acid sequence encoding a chimeric polypeptide according to claim 1; and a second nucleic acid encoding a chimeric antigen receptor or an engineered T-cell receptor.

11. A vector comprising a nucleic acid according to claim 10 or a nucleic acid construct according to claim 10.

12. A method for making a cell according to claim 7, which comprises the step of introducing: a nucleic acid sequence into a cell, the nucleic acid sequence encoding a chimeric polypeptide comprising:

an antigen-binding domain that constitutively binds to an ectodomain of a first chain of a cytokine receptor;

a transmembrane domain; and an endodomain from a second chain of the cytokine receptor;

wherein the chimeric polypeptide, when expressed in a cell that expresses the cytokine receptor, binds to an endogenous first chain of the cytokine receptor expressed in the cell, causing constitutive cytokine signalling in the cell.

13. A method for inducing constitutive cytokine signalling in a cell, which comprises the step of expressing a chimeric polypeptide according to claim 1 in the cell.

14. A method for blocking deleterious cytokine signalling in a cell, which comprises the step of expressing a chimeric polypeptide according to claim 1 in the cell, wherein the antigen binding domain constitutively binds to common gamma chain, and wherein one or more deleterious cytokine(s) signal(s) through a cytokine receptor which comprises common gamma chain.

15. A pharmaceutical composition comprising a plurality of cells according to claim 7.

16. A method for treating a disease in a subject, which comprises the step of administering a pharmaceutical composition according to claim 15 to the subject.

17. A method for treating a disease in a subject which comprises the following steps:

(i) isolation of a cell-containing sample from the subject;

(ii) transduction or transfection of cells from the sample with the nucleic acid of claim; and (iii) administering a pharmaceutical composition comprising the cells from (ii) to the subject.

18. A method according to claim 16, wherein the disease is a cancer.

19. The chimeric polypeptide according to claim 1, wherein the chimeric polypeptide further comprises a spacer that connects the antigen-binding domain with the transmembrane domain.

20. The chimeric polypeptide according to claim 19, wherein the spacer comprises an IgG1 Fc region, an IgG1 hinge region, or a CD8 stalk.

21. The chimeric polypeptide according to claim 2, wherein the first chain of the cytokine receptor is the type I cytokine receptor γ-chain.

22. The chimeric polypeptide according to claim 21, wherein the antigen binding domain comprises an scFv which comprises light chain CDRs 1-3 of SEQ ID NO: 11-13, respectively, and heavy chain CDRs 1-3 shown in SEQ ID NO: 14-16, respectively.

23. The chimeric polypeptide according to claim 21, wherein the transmembrane domain is derived from a cytokine receptor or from CD28.

24. The chimeric polypeptide according to claim 22, wherein the transmembrane domain comprises SEQ ID NO: 7, 8, 9, or 10.

25. The chimeric polypeptide according to claim 23, wherein the chimeric polypeptide further comprises a spacer that connects the antigen-binding domain with the transmembrane domain, wherein the spacer comprises an IgG1 Fc region, an IgG1 hinge region, or a CD8 stalk.

26. The chimeric polypeptide according to claim 24, wherein the chimeric polypeptide further comprises a spacer that connects the antigen-binding domain with the transmembrane domain, wherein the spacer comprises SEQ ID NO: 4, 5, or 6.

27. The chimeric polypeptide according to claim 25, wherein the endodomain of the chimeric polypeptide is from the IL-7 receptor α-chain.

28. The chimeric polypeptide according to claim 27, wherein the endodomain of the chimeric polypeptide comprises SEQ ID NO: 3.

29. A chimeric polypeptide comprising:
   an antigen-binding domain that comprises a dAb or scFv that binds to an ectodomain of a type I cytokine receptor γ-chain;
   a transmembrane domain derived from a cytokine receptor or from CD28;
   a spacer derived from an IgG1 Fc region, an IgG1 hinge region, or a CD8 stalk;
   an endodomain derived from a type I cytokine receptor α-chain or β-chain from IL-2 receptor, IL-4 receptor, IL-7 receptor, IL-9 receptor, IL-13 receptor or IL-15 receptor;
   wherein the chimeric polypeptide, when expressed in a cell that expresses the cytokine receptor, binds to an endogenous type I cytokine receptor γ-chain expressed in the cell, causing constitutive cytokine signalling in the cell.

* * * * *

UNITED STATES PATENT AND TRADEMARK OFFICE
CERTIFICATE OF CORRECTION

PATENT NO. : 11,648,274 B2
APPLICATION NO. : 16/766128
DATED : May 16, 2023
INVENTOR(S) : Martin Pulé et al.

It is certified that error appears in the above-identified patent and that said Letters Patent is hereby corrected as shown below:

In the Claims

At Column 39, Line 51, "to any preceding" should be -- to --.

At Column 40, Line 21, "signaling" should be -- signalling --.

At Column 40, Lines 27-28, "claim 10" should be -- claim 9 --.

At Column 40, Line 50, "antigen binding" should be -- antigen-binding --.

At Column 40, Line 59, "subject" should be -- subject, --.

At Column 40, Line 63, "claim;" should be -- claim 9; --.

At Column 42, Line 13, "y-chain;" should be -- γ-chain; --.

Signed and Sealed this
Second Day of January, 2024

Katherine Kelly Vidal
Director of the United States Patent and Trademark Office